United States Patent [19]

Honda et al.

[11] Patent Number: 4,560,785
[45] Date of Patent: Dec. 24, 1985

[54] PHENYLACETIC ESTER DERIVATIVES AND PROCESS FOR PREPARING THE SAME

[75] Inventors: Haruyoshi Honda, Tomisatomura; Susumu Sato, Chiba; Kazuo Isomae, Narashino; Junji Ookawa, Yokaichiba; Tsukasa Kuwamura, Yachiyo, all of Japan

[73] Assignee: SS Pharmaceutical Co., Ltd., Tokyo, Japan

[21] Appl. No.: 581,990

[22] Filed: Feb. 21, 1984

[30] Foreign Application Priority Data

Mar. 2, 1983 [JP] Japan .................................. 58-34194
Mar. 4, 1983 [JP] Japan .................................. 58-35472

[51] Int. Cl.$^4$ ............................................. C07C 69/76
[52] U.S. Cl. ........................................ 560/52; 560/21; 514/545; 260/465 D
[58] Field of Search ............... 560/52, 21; 260/465 D; 514/545

[56] References Cited

U.S. PATENT DOCUMENTS 3,741,988  6/1973  Allais et al. ............................ 560/52

FOREIGN PATENT DOCUMENTS 4003044  11/1979  Japan .................................... 560/52

*Primary Examiner*—Paul J. Killos
*Attorney, Agent, or Firm*—Oblon, Fisher, Spivak, McClelland & Maier

[57] ABSTRACT

Novel phenylacetic ester derivatives (I)

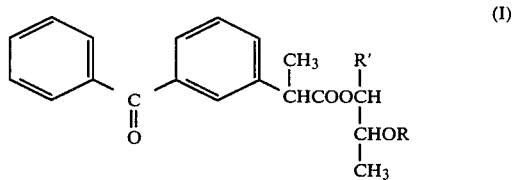

are produced by reacting ketoprofene with alkylene glycol compounds.

The derivatives (I) are useful as a nonsteroidal antiphlogistic and analgesic agent with very reduced side effects comparing with sole use of ketoprofene.

13 Claims, No Drawings

PHENYLACETIC ESTER DERIVATIVES AND PROCESS FOR PREPARING THE SAME

BACKGROUND OF THE INVENTION (i) Field of the Invention

This invention relates to novel phenylacetic ester derivatives and more particularly, to phenylacetic ester derivatives represented by the general formula (I)

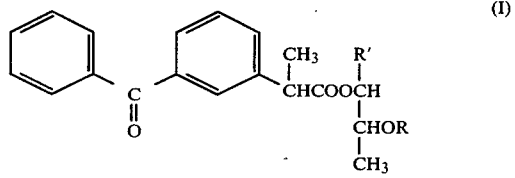

in which R represents hydrogen, a $COR_1$ group (in which $R_1$ represents an alkyl group or an alkenyl group), a

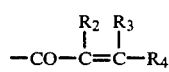

group (in which R2 represents hydrogen, a halogen atom, a cyano group, a lower alkyl group or a phenyl group, $R_3$ represents hydrogen, a lower alkyl group or a phenyl group, $R_4$ represents a phenyl group which is unsubstituted or substituted with a lower alkyl group, a lower alkyloxy group, an acyloxy group, a hydroxy group or a halogen atom), a $-CO-A-R_5$ group (in which A represents a single bond, an alkylene group having 1 or 2 carbon atoms or an alkyleneoxy group having 1 or 2 carbon atoms and $R_5$ represents a phenyl group which is unsubstituted or substituted with a lower alkyl group, a lower alkyloxy group, an acyloxy group, a hydroxy group, a halogen atom, a nitro group, a benzoyl group or an alkylenedioxy group, and R' represents hydrogen or a methyl group. The invention also relates to the preparation of these derivatives.

(ii) Description of the Prior Art

Ketoprofen is one of drugs which are now widely used, as a non-steroidal antiphlogistic and analgesic agent, in the treatment of headache, toothache, lombago, myodinia and rheumatic diseases. However, it is known that when ketoprofen is orally dosed, side effects such as gastroenteric troubles are produced accompanied by ulceration. Ketoprofen may bring about unfavorable symptoms such as congestion and hemorrhage of stomach not only in the case of long-term administration such as in the medical treatment of rheumatic diseases, but also even in short-term administration. Accordingly, limitation is placed on the manner of administration and the dose.

SUMMARY OF THE INVENTION

We have made intensive studies in order to reduce the side effects of ketoprofen and, as a result, found that phenylacetic ester derivatives of the afore-indicated formula (I) obtained by reaction between ketoprofen and alkylene glycol compounds have such a high level of antiphlogistic and analgesic action as ketoprofene but the side effects thereof are shown only in a much weaker degree than ketoprofen.

An object of the present invention is to provide novel phenylacetic ester derivatives (I) which are useful as a non-steroidal antiphlogistic and analgesic agent.

Another object of the invention is to provide a process for preparing novel phenylacetic ester derivatives (I).

DETAILED DESCRIPTION OF THE INVENTION AND PREFERRED EMBODIMENTS

The compounds (I) of the invention can be prepared utilizing a known esterification reaction by the following processes.

Process 1

Ketoprofen (II) or its reactive derivatives are reacted with alkylene glycols (III) or reactive derivatives thereof, thereby producing phenylacetic ester derivative (Ia):

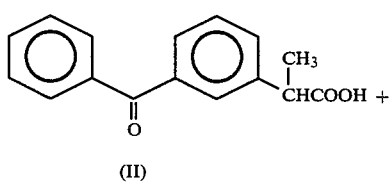

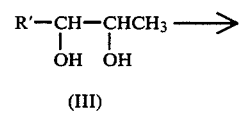

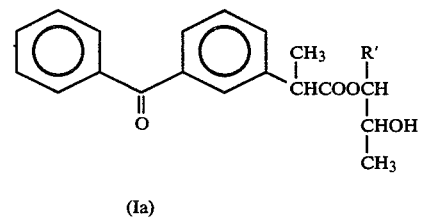

in which R' have the same meaning as defined before.

Process 2

The phenylacetic ester derivative (Ia) obtained in Process 1 is subsequently reacted with a carboxylic acid (IV) or its reactive derivatives in the presence of a condensing agent, thereby obtaining a phenylacetic ester derivative (Ib).

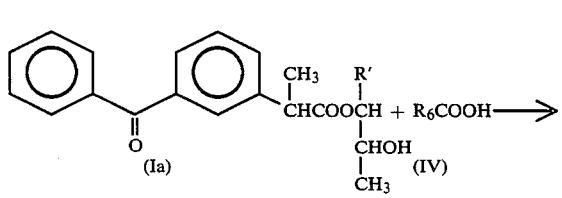

-continued

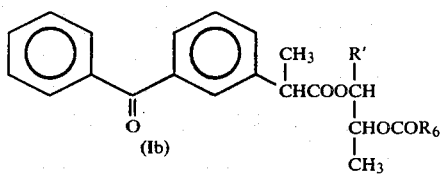

in which R₆ represents the R₁ defined before,

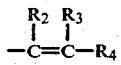

or —A—R₅, and R' has the same meaning as defined before.

Process 3

2,3-Butanediol monoester derivatives (V) are reacted with ketoprofen (II) or its reactive derivatives, thereby obtaining a phenylacetic ester derivative (Ib).

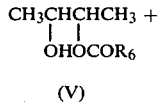

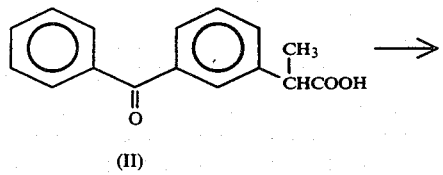

in which R₆ has the same meaning as defined before.

In the above processes, the reactive derivatives of ketoprofene (II) and the carboxylic acid (IV) are, for example, acid halides, acid anhydrides and mixed acid anhydrides.

The reaction is favorably effected in the presence of an acid eliminator such as a tertiary amine, for example, pyridine, trimethylamine, triethylamine etc.; an alkali carbonate, an alkali hydroxide, an metal hydride or the like.

The reaction is ordinarily carried out in suitable solvents which do not take part in the reaction and which include, for example, ether, tetrahydrofuran, benzene, toluene, chloroform, dichloromethane and the like.

With the reaction using a condensing agent, the reaction is favorably effected in the presence of a 2-halo-1-alkylpyridinium salt and a tertiary amine such as pyridine, triethylamine, tributylamine or the like, or a combination of diethylazodicarboxylate and triphenylphosphine. This condensation reaction is preferably conducted in solvent. Examples of such solvent include those which do not take part in the reaction and include, for example, ether, tetrahydrofuran, benzene, toluene, acetonitrile, chloroform, dichloromethane and the like.

The thus obtained compounds (I) of the invention were subjected to an antiphlogistic test with the results shown below.

PHARMACOLOGICAL ACTION (1)

Groups of ddY female mice, each consisting of 6 mice, were fasted for 16 hours. Thereafter, compounds to be tested were each dissolved in 5% dimethylsulfoxide-polysolvate 80 and orally administrated to the mice. Sixty minutes after the administration, a 5% zymosan solution was subcutaneously injected into the sole of the right leg. After 3 hours, the mice were dislocated and slaughtered, after which the right and left legs were cut off. The left leg was used as a control for determining an edema-inhibiting rate.

The results are shown in table 1.

TABLE 1

| Compound No. | Dosage (mg/kg) | Edema-inhibiting Rate (%) |
|---|---|---|
| 2 | 50 | 31 |
| 4 | " | 29 |
| 11 | " | 27 |
| 12 | " | 28 |
| 13 | " | 37 |
| 15 | " | 31 |
| 25 | " | 30 |
| Ketoprofen | " | 38 |

PHARMACOLOGICAL ACTION (2)

Groups of male Donryu rats, each weighing about 200 g and each group consisting of 7 rats, were fasted for 48 hours. Subsequently, compounds to be tested were each suspended in an aqueous 1% sodium carboxymethyl cellulose solution and orally administrated to the rats. Sixty minutes after the administration of each compound, the volume of the sole was measured by the use of a volumenometer, followed by subcutaneously injecting 0.1 ml of an aqueous 1% carrageenin physiological saline solution into the sole of the right hind leg. The degree of edema after 3 hours was compared with that of a control which was dosed with 1% sodium carboxymethylcellulose solution to determine an edema-inhibiting rate.

The results are shown in table 2.

TABLE 2

| Compound No. | Dosage (mg/kg) | Edema-inhibiting Rate (%) |
|---|---|---|
| 28 | 10 | 28.4 |
|  | 50 | 43.4 |
| 30 | 10 | 30.6 |
|  | 50 | 50.5 |
| 42 | 10 | 20.5 |
|  | 50 | 40.7 |
| 44 | 10 | 21.4 |
|  | 50 | 46.0 |
| 47 | 10 | 20.0 |
|  | 50 | 40.0 |
| Ketoprofen | 10 | 32.8 |
|  | 50 | 49.0 |

As will be apparent from Tables 1 and 2, the compounds of the present invention exhibit high edema-inhibiting rates.

The compounds of the invention were found to be weaker in degree of ulceration, which was a side effect involved in non-steroidal antiphlogistic and analgesic substances, than ketoprofen.

The present invention is particularly described by way of examples.

EXAMPLE 1 (Synthesis of Compound 1)

50.8 g of ketoprofen was suspended in 600 ml of benzene, to which was added 80 ml of thionyl chloride, followed by heating and agitating for 6 hours. After completion of the reaction, the excessive amount of thionyl chloride and benzene were distilled off under reduced pressure to obtain a light yellow liquid of the acid chloride of ketoprofen. This acid chloride was dissolved in 200 ml of absolute tetrahydrofuran and was dropped portion by portion into a mixed solution of 76 g of propylene glycol, 20 ml of pyridine and 500 ml of absolute tetrahydrofuran. After the dropping, the mixture was stirred at room temperature overnight, after which the reaction solution was subjected to distillation under reduced pressure. To the resulting residue was added 800 ml of ether, followed by washing with brine, 10% hydrochloric acid, water, sodium carbonate solution and water in this order and drying with anhydrous magnesium sulfate. The residue obtained after distillation of the ether was purified by the column chromatography (silica gel) to obtain 44.9 g (yield 71.9%) of the compound 1 in the form of a colorless liquid as indicated in table 3.

EXAMPLE 2 (Synthesis of Compound 2)

To a stirred solution of 1.56 g of the compound 1 obtained in Example 1 in 20 ml of absolute ether, was added 1 ml of pyridine, followed by dropping 5 ml of an ether solution containing 0.71 g of caproic chloride.

After the dropping, the mixture was agitated at room temperature for 4 hours and the reaction solution was washed with water, 10% hydrochloric acid, wafter, sodium carbonate solution and water in this order and dried with anhydrous magnesium sulfate. The ether was distilled off under reduced pressure and the resulting residue was purified by the column chromatography (silica gel), thereby obtaining 1.82 g (yield 88.7%) of compound 2 in the form of a colorless liquid indicated in Table 3.

EXAMPLE 3 (Synthesis of Compound 18)

1.56 g of Compound 1 obtained in Example 1, 2.62 g of triphenylphosphine and 2.06 g of p-acetoxycinnamic acid were dissolved in 60 ml of tetrahydrofuran, into which was added dropwise 10 ml of a tetrahydrofuran solution containing 1.74 g of diethylazodicarboxylate. After completion of the dropping, the mixture was agitated overnight at room temperature and the solvent was distilled off under reduced pressure. The resulting residue was mixed with ether and the insoluble matters were collected by filtration. The filtrate was subjected to distillation under reduced pressure and the residue was purified by the column chromatography (silica gel), thereby obtaining 2.37 g (yield 94.8%) of compound 18, indicated in Table 3, in the form of a light yellow liquid.

EXAMPLE 4

A number of compounds indicated in Table 3 were prepared in a similar manner as described in any of Examples 1 through 3. All the compounds obtained in these examples are shown in Table 3.

TABLE 3

| Compound No. | R (R, R' in Formula (I)) | R' | Property | NMR δ ppm (CDCl$_3$) |
|---|---|---|---|---|
| 1 | H | H | Colorless viscous liquid | 1.1(3H, d) 1.5(3H, d) 2.5(1H, s) 3.45~4.1(4H, m) 7.2~7.8(9H, m) |
| 2 | CO(CH$_2$)$_4$CH$_3$ | H | Colorless viscous liquid | 0.6~2.5(17H, m) 3.55~4.4(3H, m) 4.75~5.4(1H, m) 7.1~8.0(9H, m) |
| 3 | CO(CH$_2$)$_9$CH$_3$ | H | Colorless viscous liquid | 0.65~2.45(27H, m) 3.55~4.35(3H, m) 4.9~5.3(1H, m) 7.2~7.9(9H, m) |
| 4 | CO(CH$_2$)$_{14}$CH$_3$ | H | Colorless viscous liquid | 0.5~2.45(37H, m) 3.5~4.35(3H, m) 4.85~5.3(1H, m) 7.1~7.8(9H, m) |
| 5 | COCH(CH$_3$)—CH$_2$CH$_3$ | H | Light yellowish brown viscous liquid | 0.5~1.8(14H, m) 1.95~2.6(1H, m) 3.5~4.3(3H, m) 4.8~5.35(1H, m) 7.1~7.9(9H, m) |
| 6 | CO(CH$_2$)$_2$CH(CH$_3$)$_2$ | H | Colorless viscous liquid | 0.7~1.8(15H, m) 2.2(2H, t) 3.5~4.4(3H, m) 4.85~5.4(1H, m) 7.15~7.9(9H, m) |
| 7 | COCH=CHCH$_3$ | H | Colorless viscous liquid | 1.15(3H, d) 1.5(3H, d) 1.8(3H, d) 3.55~4.4(3H, m) 4.8~5.35(1H, m) 5.4~5.95(1H, m) 6.5~7.05(1H, m) 7.1~7.9(9H, m) |
| 8 | CO(CH$_2$)$_2$CH=CH$_2$ | H | Colorless viscous liquid | 1.1(3H, d) 1.5(3H, d) 2.1~2.5(4H, m) 3.5~4.35(3H, m) 4.7~5.3(3H, m) 5.4~6.1(1H, m) 7.2~7.9(9H, m) |
| 9 | 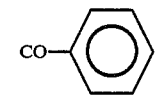 | H | Colorless viscous liquid | 1.25(3H, d) 1.5(3H, d) 3.75(1H, t) 4.3(2H, d) 5.0~5.6(1H, m) 7.0~8.2(14H, m) |
| 10 |  | H | Colorless viscous liquid | 1.1~1.7(6H, m) 2.3(3H, s) 3.75(1H, t) 4.3(2H, d) 5.0~5.6(1H, m) 7.0~8.0(13H, m) |

TABLE 3-continued

| Compound No. | R (in Formula (I)) | R' | Property | NMR δ ppm (CDCl$_3$) |
|---|---|---|---|---|
| 11 | CO—C$_6$H$_4$—OCH$_3$ | H | Colorless viscous liquid | 1.1~1.7(6H, m) 3.5~4.5(6H, m) 5.0~5.5(1H, m) 6.6~7.95(13H, m) |
| 12 | CO—C$_6$H$_4$—OCOCH$_3$ | H | Colorless viscous liquid | 1.1~1.7(6H, m) 2.2(3H, s) 3.55~4.5(3H, m) 5.0~5.55(1H, m) 6.9~8.0(13H, m) |
| 13 | CO—C$_6$H$_4$—OH | H | Colorless viscous liquid | 1.1~1.8(6H, m) 3.6~4.5(3H, m) 5.0~5.6(1H, m) 6.7~8.0(13H, m) 8.3(1H, br) |
| 14 | CO—C$_6$H$_4$—Cl | H | Colorless viscous liquid | 1.1~1.8(6H, m) 3.8(1H, t) 4.3(2H, d) 5.0~5.6 (1H, m) 7.0~8.0(13H, m) |
| 15 | CO—CH=CH—C$_6$H$_5$ | H | Colorless viscous liquid | 1.1~1.7(6H, m) 3.55~4.4(3H, m) 4.9~5.5(1H, m) 6.05~6.55(1H, m) 7.1~7.9(15H, m) |
| 16 | CO—CH=CH—C$_6$H$_4$—CH$_3$ | H | Light yellow viscous liquid | 1.1~1.8(6H, m) 2.25(3H, s) 3.5~4.4(3H, m) 4.9~5.45(1H, m) 6.0~6.5(1H, m) 6.9~7.9(14H, m) |
| 17 | CO—CH=CH—C$_6$H$_4$—OCH$_3$ | H | Light yellow viscous liquid | 1.1~1.7(6H, m) 3.5~4.4(6H, m) 4.9~5.4(1H, m) 6.0~6.5(1H, m) 7.1~7.9(14H, m) |
| 18 | CO—CH=CH—C$_6$H$_4$—OCOCH$_3$ | H | Light yellow viscous liquid | 1.0~1.7(6H, m) 2.2(3H, s) 3.55~4.4(3H, m) 4.9~5.4(1H, m) 6.0~6.5(1H, m) 6.9~7.9(14H, m) |
| 19 | CO—CH=CH—C$_6$H$_4$—OH | H | Light yellow viscous liquid | 1.0~1.8(6H, m) 3.85(1H, q) 4.0~4.5(2H, m) 5.0~5.5(1H, m) 5.9~6.5(1H, m) 6.6~8.1(15H, m) |
| 20 | CO—CH=CH—C$_6$H$_4$—Cl | H | Light yellow viscous liquid | 1.1~1.75(6H, m) 3.6~4.4(3H, m) 5.0~5.5(1H, m) 6.0~6.5(1H, m) 7.1~7.9(14H, m) |
| 21 | COC(CH$_3$)=CH—C$_6$H$_5$ | H | Light yellow viscous liquid | 1.25(3H, d) 1.55(3H, d) 2.1(3H, d) 3.8(1H, q) 4.1~4.35(2H, m) 4.95~5.5(1H, m) 7.1~7.9(15H, m) |
| 22 | C$_6$H$_5$—COC=CH—C$_6$H$_5$ | H | Light yellow viscous liquid | 1.0~1.7(6H, m) 3.4~4.4(3H, m) 4.9~5.5(1H, m) 6.9~7.85(20H, m) |
| 23 | COCH=C(CH$_3$)—C$_6$H$_5$ | H | Light yellow viscous liquid | 1.0~1.7(6H, m) 2.4~2.6(3H, m) 3.5~4.3(3H, m) 4.9~5.5(1H, m) 5.8~6.2(1H, m) 7.1~7.9(14H, m) |

TABLE 3-continued

| Compound No. | R (R, R' in Formula (I)) | R' | Property | NMR δ ppm (CDCl₃) |
|---|---|---|---|---|
| 24 | COCH=C-(biphenyl) | H | Light yellow viscous liquid | 0.9~1.7(6H, m) 3.6~4.3(3H, m) 4.8~5.3(1H, m) 6.1~6.4(1H, m) 6.9~7.9(19H, m) |
| 25 | COCH₂-(phenyl) | H | Light yellow viscous liquid | 1.1(3H, d) 1.45(3H, d) 3.4~4.3(5H, m) 4.75~5.3 (1H, m) 7.0~7.9(14H, m) |
| 26 | COCH₂O-(phenyl) | H | Light yellow viscous liquid | 1.15(3H, d) 1.45(3H, d) 3.5~4.6(5H, m) 4.8~5.45 (1H, m) 7.1~7.9(14H, m) |
| 27 | COCH(CH₃)-(phenyl)-C(=O)-(phenyl) | H | Light yellow viscous liquid | 0.9~1.7(9H, m) 3.4~4.4(4H, m) 4.8~5.3(1H, m) 7.0~7.9(18H, m) |

EXAMPLE 5 (Synthesis of Compound 28)

50.80 g of ketoprofen was suspended in 600 ml of benzene, to which was added 80 ml of thionyl chloride, followed by heating and agitating for 6 hours. After completion of the reaction, the thionyl chloride and benzene in excess were distilled off under reduced pressure to obtain an acid chloride of ketoprofen in the form of a light yellow liquid.

This acid chloride was dissolved in 200 ml of absolute ether and was dropped portion by portion into a mixed solution of 18 g of 2,3-butanediol, 20 ml of pyridine and 500 ml of absolute ether. After completion of the dropping, the mixture was agitated at room temperature for 5 hours, after which the reaction solution was washed with water, 10% hydrochloric acid, sodium carbonate solution and water in this order, followed by drying with anhydrous magnesium sulfate. The residue obtained after removal of the ether by distillation was purified by the column chromatography (silica gel), thereby obtaining 40.10 g (yield 61.5%) of compound 28, indicated in Table 4, in the form of a colorless liquid.

EXAMPLE 6 (Synthesis of Compound 29)

1.63 g of compound 28 was dissolved in 20 ml of absolute ether, to which was added 1 ml of pyridine, followed by dropping 5 ml of an ether solution containing 0.71 g of caproic chloride while agitating under ice-cooling conditions. The mixture was further stirred at the temperature for 30 minutes and, after returning to room temperature, was agitated for further 4 hours. Thereafter, the reaction solution was washed with water, 10% hydrochloric acid, water, sodium carbonate solution and water in this order, followed by drying with anhydrous magnesium sulfate. The ether was distilled off under reduced pressure and the resulting residue was purified by the column chromatography (silica gel) to obtain 1.70 g (yield 80.0%) of compound 29, indicated in Table 4, in the form of a colorless liquid.

EXAMPLE 7 (Synthesis of Compound 59)

1.80 g of 2,3-butanediol was dissolved in 40 ml of tetrahydrofuran, to which was added 2 ml of pyridine, followed by dropping 10 ml of a tetrahydrofuran containing 2.42 g of alpha-phenylcinnamic chloride while agitating under ice-cooling conditions. The mixture was agitated at the temperature for 30 minutes and, after returning to room temperature, was agitated for further 5 hours. The solvent was distilled off under reduced pressure and the residue was again dissolved in ether. The ether phase was washed with water, 10% hydrochloric acid, water, sodium carbonate solution and water, followed by drying with anhydrous magnesium sulfate. The ether was distilled off under reduced pressure and the resulting residue was purified by the column chromatography (silica gel) to obtain 2.01 g (yield 67.6%) of a colorless liquid monoester product. This monoester product was dissolved in 20 ml of absolute ether, to which was added 1 ml of pyridine, followed by dropping 5 ml of an ether solution containing 1.85 g of an acid chloride of ketoprofene while agitating under ice-cooling conditions. The mixture was agitated at the temperature for 30 minutes and, after returning to room temperature, was further agitated overnight. Subsequently, the reaction solution was washed with water, 10% hydrochloric acid, water, sodium carbonate solution and water and dried with anhydrous magnesium sulfate. The ether was distilled off under reduced pressure and the resulting residue was purified by the column chromatography (silica gel) to obtain 3.12 g (yield 86.8%) of compound 59, indicated in Table 4, in the form of a light yellow liquid.

EXAMPLE 8 (Synthesis of Compound 55)

1.63 g of compound 28, 2.62 g of triphenylphosphine and 2.06 g of p-acetoxycinnamic acid were dissolved in 60 ml of tetrahydrofuran, into which was dropped 10 ml of a tetrahydrofuran solution containing 1.74 g of diethylazodicarboxylate. After completion of the dropping, the mixture was agitated at room temperature overnight, after which the solvent was distilled off under reduced pressure. To the resulting residue was added ether, followed by removing the insoluble matters by filtration. The filtrate was distilled off under reduced pressure and the residue was purified by the column chromatography to obtain 2.25 g (yield 87.5%) compound 55, indicated in Table 4, in the form of a light yellow liquid.

EXAMPLE 9 (Synthesis of Compound 53)

0.77 g of 2-chloro-1-methylpyridinium iodide was suspended in 10 ml of toluene, to which was added a solution, in 10 ml of toluene, of 0.82 g of compound 28, 0.41 g of p-methylcinnamic acid and 1.1 g of tributylamine, followed by heating and agitating for 3 hours. Thereafter, the solvent was distilled off under reduced pressure and the resulting residue was purified by column chromatography (silica gel) to obtain 0.36 g (yield 30.6%) of compound 53, indicated in Table 4, in the form of a light yellow liquid.

TABLE 4

| Compound No. | R (in Formula (I)) | R' | Property | NMR δppm (CDCl$_3$) |
|---|---|---|---|---|
| 28 | H | CH$_3$ | Colorless viscous liquid | 0.9~1.35(6H,m) 1.5(3H,d) 1.9(1H,s) 3.4~4.0 (2H,m) 4.5~5.0(1H,m) 7.2~7.9(9H,m) |
| 29 | CO(CH$_2$)$_4$CH$_3$ | CH$_3$ | Colorless viscous liquid | 0.7~1.9(18H,m) 2.15(2H,t) 3.8(1H,q) 4.7~5.1(2H,m) 7.25~7.90(9H,m) |
| 30 | CO(CH$_2$)$_5$CH$_3$ | CH$_3$ | Colorless viscous liquid | 0.7~1.9(20H,m) 2.1(2H,t) 3.8(1H,q) 4.7~5.2(2H,m) 7.2~7.95(9H,m) |
| 31 | CO(CH$_2$)$_6$CH$_3$ | CH$_3$ | Colorless viscous liquid | 0.7~1.9(22H,m) 2.1(2H,t) 3.75(1H,q) 4.7~5.2(2H,m) 7.3~7.95(9H,m) |
| 32 | CO(CH$_2$)$_7$CH$_3$ | CH$_3$ | Colorless viscous liquid | 0.7~1.8(24H,m) 2.15(2H,t) 3.8(1H,q) 4.7~5.2(2H,m) 7.3~7.95(9H,m) |
| 33 | CO(CH$_2$)$_8$CH$_3$ | CH$_3$ | Colorless viscous liquid | 0.65~1.85(26H,m) 2.1(2H,t) 3.8(1H,q) 4.7~5.2(2H,m) 7.25~7.9(9H,m) |
| 34 | CO(CH$_2$)$_9$CH$_3$ | CH$_3$ | Colorless viscous liquid | 0.7~1.9(28H,m) 2.2(2H,t) 3.8(1H,q) 4.7~5.2 (2H,m) 7.3~7.85(9H,m) |
| 35 | CO(CH$_2$)$_{12}$CH$_3$ | CH$_3$ | Colorless viscous liquid | 0.7~1.8(34H,m) 2.15(2H,t) 3.75(1H,q) 4.65 ~5.2(2H,m) 7.3~7.9(9H,m) |
| 36 | CO(CH$_2$)$_{14}$CH$_3$ | CH$_3$ | Colorless crystals | 0.6~2.4(40H,m) 3.75(1H,q) 4.7~5.2(2H,m) 7.3~7.9(9H,m) |
| 37 | COCH(CH$_3$)CH$_2$CH$_3$ | CH$_3$ | Colorless viscous liquid | 0.5~2.4(18H,m) 3.8(1H,q) 4.3~5.15(2H,m) 7.3~7.85(9H,m) |
| 38 | CO(CH$_2$)$_2$CH(CH$_3$)$_2$ | CH$_3$ | Colorless viscous liquid | 0.6~2.45(20H,m) 3.75(1H,q) 4.6~5.2(2H,m) 7.3~7.85(9H,m) |
| 39 | COCH=CHCH$_3$ | CH$_3$ | Light yellow viscous liquid | 0.9~2.0(12H,m) 3.8(1H,q) 4.7~5.2(2H,m) 5.4~5.9(1H,m) 6.6~7.9(10H,m) |
| 40 | CO(CH$_2$)$_2$CH=CH$_2$ | CH$_3$ | Light yellow viscous liquid | 0.8~1.35(6H,m) 1.5(3H,d) 1.9~2.5(4H,m) 3.8(1H,q) 4.6~5.25(4H,m) 5.3~6.1(1H,m) 7.0~7.9(9H,m) |
| 41 | COCH=CH(CH$_2$)$_6$CH$_3$ | CH$_3$ | Light yellow viscous liquid | 0.6~2.4(24H,m) 3.75(1H,q) 4.7~5.2(2H,m) 5.4~5.9 (1H,m) 6.6~7.9(10H,m) |
| 42 | CO(CH$_2$)$_8$CH=CH$_2$ | CH$_3$ | Colorless viscous liquid | 0.9~2.5(25H,m) 3.8(1H,q) 4.6~5.2(4H,m) 5.4 ~6.1(1H,m) 7.1~7.9(9H,m) |
| 43 | CO—C$_6$H$_5$ | CH$_3$ | Colorless viscous liquid | 1.1~1.7(9H,m) 3.8(1H,q) 4.85~5.5(2H,m) 7.2~8.3(14H,m) |
| 44 | CO—C$_6$H$_4$—CH$_3$ | CH$_3$ | Colorless viscous liquid | 1.15~1.7(9H,m) 2.3(3H,s) 3.75(1H,q) 4.8~5.4(2H,m) 7.0~7.95(13H,m) |
| 45 | CO—C$_6$H$_4$—OCH$_3$ | CH$_3$ | Colorless viscous liquid | 1.0~1.7(9H,m) 3.6~4.0(4H,m) 4.85~5.3(2H,m) 6.7~8.0(13H,m) |
| 46 | CO—C$_6$H$_4$—OCOCH$_3$ | CH$_3$ | Colorless viscous liquid | 1.0~1.7(9H,m) 2.2(3H,s) 3.75(1H,q) 4.8~5.35 (2H,m) 6.9~8.1(13H,m) |
| 47 | CO—C$_6$H$_4$—OH | CH$_3$ | Light yellow viscous liquid | 1.0~1.7(9H,m) 3.8(1H,q) 4.9~5.4(2H,m) 6.6~8.0(13H,m) 8.3(1H,br) |
| 48 | CO—C$_6$H$_4$—Cl | CH$_3$ | Colorless viscous liquid | 1.0~1.7(9H,m) 3.8(1H,q) 4.9~5.4(2H,m) 7.0~8.0(13H,m) |

TABLE 4-continued

| Compound No. | R (in Formula (I)) | R' | Property | NMR δppm (CDCl₃) |
|---|---|---|---|---|
| 49 | CO—C₆H₄—NO₂ | CH₃ | Light yellow viscous liquid | 1.1~1.75(9H,m) 3.85(1H,q) 4.9~5.5(2H,m) 7.2~8.4(13H,m) |
| 50 | CO—C₆H₃(OCH₂O) (methylenedioxyphenyl) | CH₃ | Light yellow viscous liquid | 1.0~1.8(9H,m) 3.75(1H,q) 4.8~5.4(2H,m) 5.85(2H,s) 6.55~6.8(1H,m) 7.05~7.85(11H,m) |
| 51 | CO—C₆H₂(OCH₃)₃ (3,4,5-trimethoxyphenyl) | CH₃ | Light yellow viscous liquid | 1.0~1.7(9H,m) 3.8(10H,s) 4.8~5.3(2H,m) 7.0~7.8(11H,m) |
| 52 | CO—CH=CH—C₆H₅ | CH₃ | Colorless viscous liquid | 1.0~1.4(6H,m) 1.5(3H,d) 3.8(1H,q) 4.8~5.3(2H,m) 6.1~6.5(1H,m) 7.1~7.9(15H,m) |
| 53 | CO—CH=CH—C₆H₄—CH₃ | CH₃ | Light yellow viscous liquid | 0.9~1.4(6H,m) 1.5(3H,d) 2.3(3H,s) 3.75(1H,q) 4.7~5.3(2H,m) 6.1~6.4(1H,m) 6.95~7.85(14H,m) |
| 54 | CO—CH=CH—C₆H₄—OCH₃ | CH₃ | Light yellow viscous liquid | 0.9~1.4(6H,m) 1.5(3H,d) 3.55~3.9(4H,m) 4.7~5.25(2H,m) 5.95~6.3(1H,m) 6.8(2H,d) 7.2~7.8(12H,m) |
| 55 | CO—CH=CH—C₆H₄—OCOCH₃ | CH₃ | Colorless viscous liquid | 1.0~1.4(6H,m) 1.5(3H,d) 2.2(3H,s) 3.8(1H,q) 4.8~5.3(2H,m) 6.0~6.35(1H,m) 6.9~7.9(14H,m) |
| 56 | CO—CH=CH—C₆H₄—OH | CH₃ | Light yellow viscous liquid | 0.9~1.7(9H,m) 3.8(1H,q) 4.8~5.3(2H,m) 6.0~6.3(1H,m) 6.5~8.0(14H,m) |
| 57 | CO—CH=CH—C₆H₄—Cl | CH₃ | Light yellow viscous liquid | 0.9~1.4(9H,m) 1.55(3H,d) 3.8(1H,q) 4.75~5.3(2H,m) 6.05~6.40(1H,m) 7.0~7.8(14H,m) |
| 58 | CO—C(CH₃)=CH—C₆H₅ | CH₃ | Light yellow viscous liquid | 1.0~1.4(6H,m) 1.5(3H,d) 2.05(3H,d) 3.8(1H,q) 4.7~5.3(2H,m) 7.0~7.8(15H,m) |
| 59 | CO—C(C₆H₅)=CH—C₆H₅ | CH₃ | Light yellow viscous liquid | 0.9~1.35(6H,m) 1.45(3H,d) 3.75(1H,q) 4.7~5.3(2H,m) 6.9~7.9(20H,m) |
| 60 | CO—C(CN)=CH—C₆H₅ | CH₃ | Yellow viscous liquid | 0.9~1.8(9H,m) 3.8(1H,q) 4.8~5.4(2H,m) 7.1~8.2(15H,m) |
| 61 | CO—C(F)=CH—C₆H₅ | CH₃ | Colorless viscous liquid | 0.9~1.8(9H,m) 3.75(1H,q) 4.8~5.4(2H,m) 6.55~6.85(1H,m) 7.0~7.9(14H,m) |
| 62 | CO—CH=C(CH₃)—C₆H₅ | CH₃ | Light yellow viscous liquid | 0.9~1.8(9H,m) 2.4~2.65(3H,m) 3.75(1H,q) 4.7~5.3(2H,m) 5.8~6.15(1H,m) 7.1~7.8(14H,m) |
| 63 | CO—CH=C(C₆H₅)₂ | CH₃ | Light yellow viscous liquid | 0.8~1.2(6H,m) 1.5(3H,d) 3.75(1H,q) 4.6~5.1(2H,m) 6.3(1H,s) 7.0~7.9(19H,m) |
| 64 | CO—CH₂—C₆H₅ | CH₃ | Light yellow viscous liquid | 0.95~1.15(6H,m) 1.45(3H,d) 3.35~3.9(3H,m) 4.7~5.15(2H,m) 7.1~7.8(14H,m) |
| 65 | CO—CH₂O—C₆H₅ | CH₃ | Colorless viscous liquid | 1.0~1.2(6H,m) 1.45(3H,d) 3.75(1H,q) 4.0(2H,s) 4.75~5.2(2H,m) 6.7~7.8(14H,m) |

TABLE 4-continued

| Compound No. | R, R' in Formula (I) R | R' | Property | NMR δppm (CDCl₃) |
|---|---|---|---|---|
| 66 | COCHO—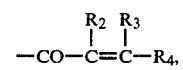 with CH₃ | CH₃ | Colorless viscous liquid | 0.8~1.3(6H,m) 1.35~1.8(6H,m) 3.75(1H,q) 4.4~5.2(3H,m) 6.6~7.8(14H,m) |
| 67 | COCH₂CH₂—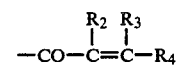 | CH₃ | Light yellow viscous liquid | 0.8~1.25(6H,m) 1.45(3H,d) 2.1~3.0(4H,m) 3.8(1H,q) 4.6~5.2(2H,m) 6.9~7.9(14H,m) |
| 68 | COCH—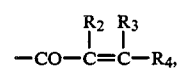 with CH₃ and C(=O)phenyl | CH₃ | Light yellow viscous liquid | 0.8~1.7(12H,m) 3.5~4.0(2H,m) 4.6~5.2(2H,m) 7.2~8.0(18H,m) |

What is claimed is:

1. A phenylacetic ester derivative of formula (I):

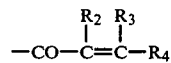

(I)

wherein R is hydrogen; a COR₁ group, wherein R₁ is alkyl or alkenyl; a

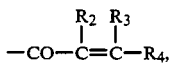

group, wherein R₂ is hydrogen, halogen, cyano, lower alkyl or phenyl, R₃ is hydrogen, lower alkyl or phenyl, R₄ is phenyl or phenyl substituted by lower alkyl, lower alkyloxy, acyloxy, hydroxy or halogen; or —CO—A—R₅, wherein A is a single bond, $C_1$-$C_2$ alkylene or $C_1$-$C_2$ alkyleneoxy, and R₅ is phenyl or phenyl substituted by lower alkyl, lower alkyloxy, acyloxy, hydroxy, halogen, nitro, benzoyl or alkylenedioxy; and R' is hydrogen or methyl.

2. The phenylacetic ester derivative of claim 1, wherein said substituent R₁ is pentyl, decyl, pentadecyl, sec-butyl or 3-methylbutyl, and R' is hydrogen.

3. The phenylacetic ester derivative of claim 1, wherein R' is hydrogen and said substituent R₁ is propenyl or butenyl.

4. The phenylacetic ester derivative of claim 1, wherein, in said —CO—A—R₅ group, substituent R₅ is phenyl, methylphenyl, methoxyphenyl, acetoxyphenyl, hydroxyphenyl or chlorophenyl, and group A is a single bond, and R' is hydrogen.

5. The phenylacetic ester derivative of claim 1, wherein, in said $$-CO-\underset{R_2}{\overset{R_3}{C}}=\overset{}{C}-R_4,$$

group, both R₂ and R₃ are hydrogen and R₄ is one of the R₅ radicals of claim 4, and R' is hydrogen.

6. The phenylacetic ester derivative of claim 1, wherein, in group $$-CO-\underset{R_2}{\overset{R_3}{C}}=\overset{}{C}-R_4,$$

R₂ is methyl while R₃ is hydrogen and R₄ is phenyl, R₂ is phenyl while R₃ is hydrogen and R₄ is phenyl, R₂ is hydrogen while R₃ is methyl and R₄ is phenyl, or R₂ is hydrogen while R₃ and R₄ are each phenyl, and R' is hydrogen.

7. The phenylacetic ester derivative of claim 1, wherein, in group —CO—A—R₅, group A is methylene or methyleneoxy while R₅ is phenyl, or group A is ethylidene while R₅ is benzoyl substituted phenyl and R' is hydrogen.

8. The phenylacetic ester of claim 1, wherein R₁ is sec-butyl, pentyl, 3-methylbutyl, hexyl, heptyl, octyl, nonyl, decyl, tridecyl, or pentadecyl, and R' is methyl.

9. The phenylacetic ester of claim 1, wherein R₁ is propenyl, butenyl, nonenyl, or decenyl and R' is methyl.

10. The phenylacetic ester of claim 1, wherein R₁ is phenyl, methylphenyl, methoxyphenyl, acetoxyphenyl, hydroxyphenyl, chlorophenyl, nitrophenyl, methylenedioxyphenyl or trimethoxyphenyl, and R' is methyl.

11. The phenylacetic ester of claim 1, wherein, in group $$-CO-\underset{R_2}{\overset{R_3}{C}}=\overset{}{C}-R_4$$

both R₂ and R₃ are hydrogen and R₄ is phenyl, methylphenyl, methoxyphenyl, acetoxyphenyl, hydroxyphenyl or chlorophenyl, and R' is methyl.

12. The phenylacetic ester of claim 1, wherein, in group $$-CO-\underset{R_2}{\overset{R_3}{C}}=\overset{}{C}-R_4,$$

R₂ is methyl while R₃ is hydrogen and R₄ is phenyl, R₂ is phenyl while R₃ is hydrogen and R₄ is phenyl, R₂ is cyano while R₃ is hydrogen and R₄ is phenyl, R₂ ia fluoro while R₃ is hydrogen and R₄ is phenyl, R₂ is hydrogen while R₃ and R₄ are both phenyl or R₂ is hydrogen while R₃ is methyl and R₄ is phenyl and R' is methyl.

13. The phenylacetic ester of claim 1, wherein, in group —CO—A—R₅, A is methylene and R₅ is phenyl, A is methyleneoxy and R₅ is phenyl, A is ethylideneoxy and R₅ is phenyl, A is ethylene and R₅ is phenyl or A is ethylidene and R₅ is benzoyl substituted phenyl, and R' is methyl.

* * * * *